United States Patent [19]
Webb

[11] Patent Number: 5,799,788
[45] Date of Patent: Sep. 1, 1998

[54] SUTURE NEEDLE PARK AND COLLECTOR

[75] Inventor: Nicholas J. Webb, Wrightwood, Calif.

[73] Assignee: Talon Medical Ltd., San Antonio, Tex.

[21] Appl. No.: 950,251

[22] Filed: Oct. 14, 1997

[51] Int. Cl.[6] ..................................................... A61B 17/04
[52] U.S. Cl. ............................................. 206/366; 206/380
[58] Field of Search .................................. 206/380, 381, 206/382, 383, 63.3, 443, 822, 365, 366; 220/908, 909, 910

[56] References Cited

U.S. PATENT DOCUMENTS

| | | | |
|---|---|---|---|
| 3,727,658 | 4/1973 | Eldridge, Jr. | 150/52 R |
| 3,944,009 | 3/1976 | Eldridge, Jr. | 206/350 |
| 4,494,652 | 1/1985 | Nelson et al. | 206/366 |
| 4,591,048 | 5/1986 | Eldridge, Jr. | 206/63.3 |
| 5,180,053 | 1/1993 | Cascio et al. | 206/63.3 |
| 5,181,609 | 1/1993 | Spielmann et al. | 206/366 |
| 5,316,142 | 5/1994 | Jain | 206/370 |
| 5,437,362 | 8/1995 | Sinn | 206/63.3 |
| 5,472,081 | 12/1995 | Kilgrow et al. | 206/63.3 |
| 5,503,266 | 4/1996 | Kalbfeld et al. | 206/63.3 |
| 5,590,774 | 1/1997 | Roberts | 206/63.3 |
| 5,617,952 | 4/1997 | Kranendonk | 206/63.3 |

*Primary Examiner*—Jacob K. Ackun
*Attorney, Agent, or Firm*—David P. Gordon; David S. Jacobson; Thomas A. Gallagher

[57] ABSTRACT

A suture needle holder includes a hollow holder portion which is preferably molded from a clear plastic, and a base portion coupled to a lower portion of the holder portion. A lower side of the base portion is provided with an adhesive. The holder portion is provided with at least one needle park which can be integrally molded with the holder portion. The holder portion also includes an opening through which used suture needles can be disposed into the hollow holder portion. The surgeon is able to see into the clear holder portion and make an accurate count of how many suture needles have been used. The adhesive on the base member enables the holder to be positioned on the surgical drape and prevents unintentional movement of the holder, and further facilitates single-handed use of the holder. In a preferred embodiment, the hollow holder portion is shaped like a hexagonal frustum and includes a needle park on each of its six sloped faces. Each needle park is formed by two inwardly angled walls, the walls able to frictionally engage the shaft of a suture needle. The holder portion is provided with a raised portion around which suture material may be thread to assist a physician in tying off suture. The opening is provided on the raised portion and includes a tapered entryway which prevents disposed needles from exiting the opening.

20 Claims, 3 Drawing Sheets

SUTURE NEEDLE PARK AND COLLECTOR

BACKGROUND OF THE INVENTION

1. Field of the Invention

This invention relates broadly to devices for holding and disposing of sharp surgical implements. More particularly, this invention relates to a combined holder and disposal container for suture needles.

2. State of the Art

During surgery, a surgeon often uses suture needles as part of an operation and to close entry wounds. A suture needle is a small, typically sickle-shaped needle having a length of suture tied through the eye of the needle. As a surgeon works to close the wounds, the surgeon often desires to park the needle, i.e., to temporarily place the needle into a holder, so that an interstitial procedure better performed with two unencumbered hands may be performed. For example, the surgeon is better able to tie off pieces of suture at the wound closure with two free hands.

After a needle has been used, it is desirable to safely dispose of the needle to prevent unintended sticking. The Federal Occupational Safety and Health Administration has widely recognized this concern and the related potential of harm to health care workers, as such needle sticking poses the risk of cross-contamination of threatening diseases, such as HIV and hepatitis. As a result, standards in health care mandate that surgical instruments be counted both pre- and post-operatively to ensure that instruments have not been left inside the human body.

Currently, a surgeon has three options when he or she desires to park a suture needle. One, the surgeon can use a currently available rigid foam park in which the sharp distal tip of the suture needle may be impaled to hold the needle. However, the foam tends to quickly dull the distal tip and make the continuing procedure more difficult for the surgeon and more dangerous for a patient. Second, the surgeon can use a fabric park such as the SutureMate® marketed by Surgical Safety Products Inc., of Sarasota, Fla. However, the SutureMate® requires that the needle be parked between particular stitches sewn into the fabric park, and is not convenient to use. As a result, many surgeons tend to choose the third option, which is to not park the needle. Rather the needle is cupped in one hand, only partially freeing the fingers of the hand cupping the needle, making the performance of interstitial procedures not directly involving the needle more difficult. This option further poses a risk to the surgeon, as the surgeon may receive inadvertent stab wounds and can thereby be exposed to blood-borne pathogens. Moreover, none of these options addresses providing a suitable safe means for disposing of the suture needles in a manner which permits counting of the needles.

While relatively large containers for the disposal of a relatively large number of sharps are well known, e.g., the container disclosed in U.S. Pat. No. 4,494,652 to Nelson et al., it is preferable to have a disposal container which is relatively small and provided solely for the suture needles of a current operation. The use of such a large disposal container would result in unavoidable waste, as counting of the disposed suture needles to ensure the proper number of pre- and post-operative needles (determined by the number of empty packages matched against the number of suture needles in the disposal container) requires a new container with each surgical procedure.

A number of small needle collection devices have been proposed or used. For example, U.S. Pat. No. 3,727,658 to Eldridge, Jr., discloses a foldable magnetic receiver which magnetically traps metallic surgical implements such as suture needles, and U.S. Pat. No. 3,944,069 also to Eldridge, Jr., discloses another foldable receiver. However, the receivers do not safely enclose the suture needles, and in order to count the needles used, the devices must be kept open, until surgery is complete. As a result, as each used suture needle is placed into the receiver, opportunity exists for unintentional hand pricking by a sharp needle located in the trap. U.S. Pat. No. 4,591,048 to Eldridge, Jr., and U.S. Pat. No. 5,316,142 to Jain each disclose used needle collectors having numbered parks in which to place used needles. The numbered parks allow a surgeon to keep track of the number of needles used. However, each has an open design, being made from foam and sponge-plastic, respectively, and presents the opportunity for hand pricking. In addition, in order to place the needle into each of the collectors, two hands are required to compartmentalize the needle. As the surgeon may have one hand occupied, this can be inconvenient. U.S. Pat. No. 5,590,774 to Roberts discloses a cup-like suture needle container having several radial compartments in which needles can be placed, a rotatable locking lid which provides entry only into a single compartment at a time, and a handle. However, the device requires two hands to operate, one to hold the handle and the other to rotate the lid to close one compartment and open another.

Moreover, the art does not provide any device which provides both a needle park and a used needle collector within the same device. In addition, none of the devices of the prior art are adapted to remain stationary, and not move around, while in use. Also, none of the devices of the prior art assist a surgeon in tying off suture.

SUMMARY OF THE INVENTION

It is therefore an object of the invention to provide a single device which acts as a suture needle park and collection device.

It is also an object of the invention to provide a device that can hold suture needles in a manner which prevents inadvertent stab wounds and which will not dull the needles.

It is another object of the invention to provide a needle collection device which permits an accurate counting of used suture needles post-operatively in order to ensure that suture needles have not been left in the human body.

It is an additional object of the invention to provide a device that can be used to safely dispose of suture needles.

It is also an object of the invention to provide a suture needle collecting and parking device which will remain stationary while in use.

It is a further object of the invention to provide a device that can assist a surgeon in tying off sutures.

In accord with these objects, which will be discussed in detail below, a suture needle holder for holding and collecting suture needles is provided. The suture needle holder generally includes a hollow, preferably frustum-shaped, holder portion which is preferably molded from a clear plastic, and a base portion coupled to a lower portion of the holder portion. A lower side of the base portion is preferably provided with an adhesive. The holder portion is provided with at least one needle park which is preferably integrally molded with the holder portion. The holder portion also includes an opening through which used suture needles can be disposed of into the hollow holder portion.

It will be appreciated that a surgeon is able to see into the clear holder portion and make an accurate count of how many suture needles have been used. Furthermore, the adhesive on the base portion enables the holder to be positioned on the surgical drape and prevents unintentional movement of the holder. In addition, the adhesion of the holder to the drape facilitates single-handed use of the holder and allows the surgeon to keep one hand free while using the holder.

According to a first and preferred embodiment of the invention, the hollow holder portion is shaped like a hexagonal frustum and includes a needle park on each of its six sloped faces. Each needle park is formed by two inwardly angled walls which are capable of frictionally engaging the shaft of a suture needle. The upper surface of the holder portion is preferably provided with a raised portion having a circumferential channel around which suture material may be thread. The raised portion and channel may be used to assist a physician in tying off suture. The opening through which used needles may be disposed into the interior of the holder portion is provided on the raised portion and includes a tapered entryway which prevents needles from exiting the opening.

According to a second embodiment of the invention, each needle park of the holder portion is generally formed from two walls each of which has a lateral side coupled to the same sloping face, and a medial free side. The walls are inwardly angled and biased toward each other. The needles may be frictionally held between the free sides of the inwardly angled walls and, if desired, may be further pushed through the opening between the walls to be disposed of within the holder portion.

Additional objects and advantages of the invention will become apparent to those skilled in the art upon reference to the detailed description taken in conjunction with the provided figures.

DETAILED DESCRIPTION OF THE PREFERRED EMBODIMENTS

Figure 1:
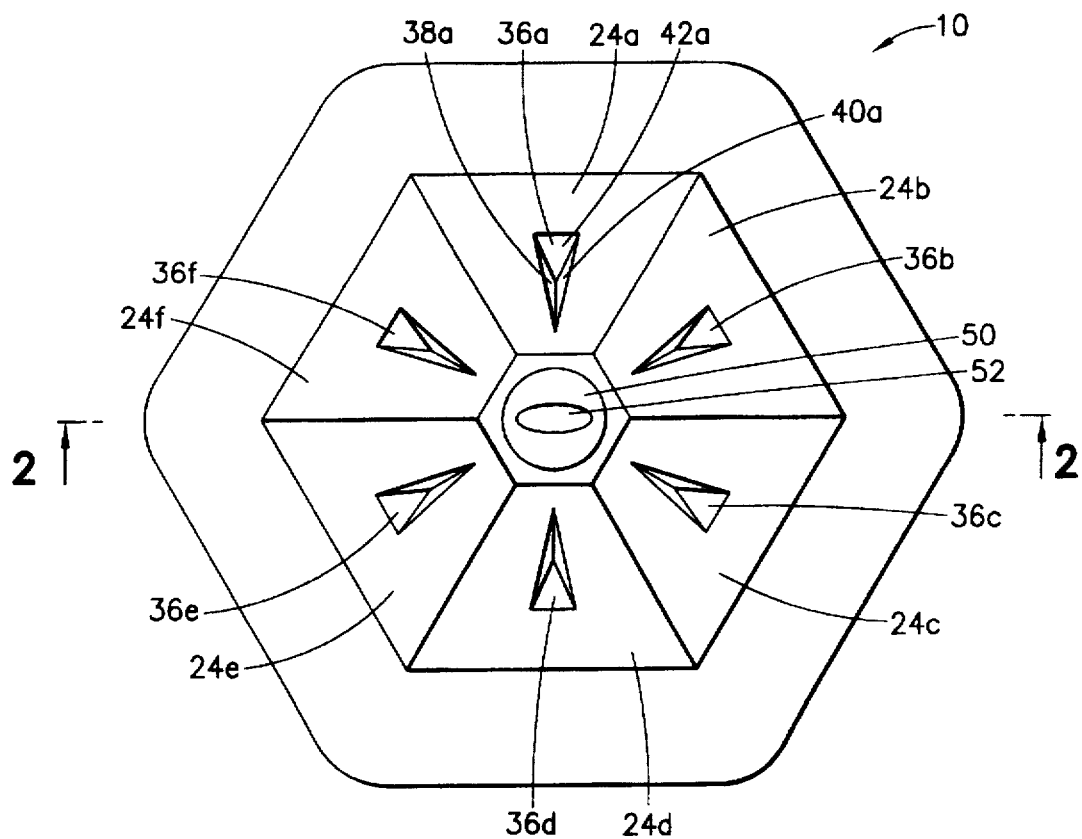
FIG. 1 is top view of a first embodiment of a suture needle holder according the invention.
Figure 2:
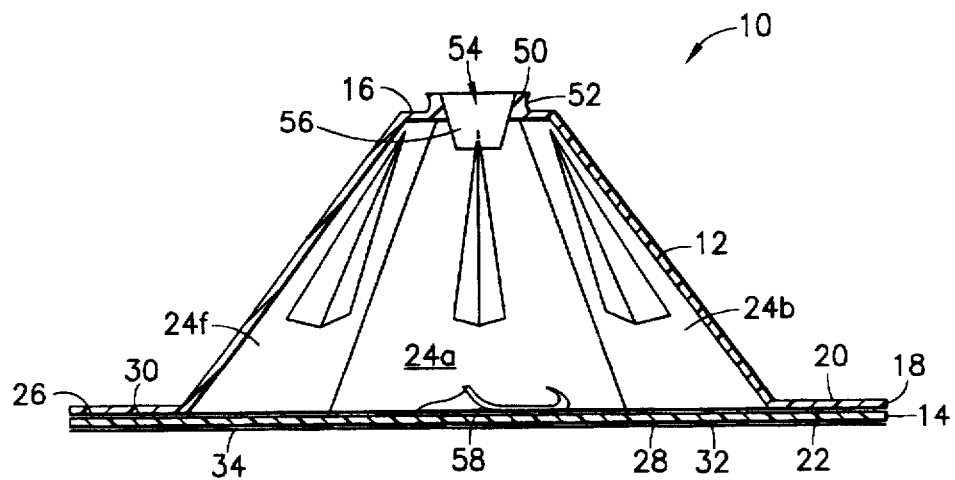
FIG. 2 is a cross section through line 2—2 in FIG. 1.

Turning now to FIGS. 1 and 2, a first embodiment of a suture needle holder 10 is shown. The suture needle holder 10 generally includes a hollow frustum-shaped holding member 12 and a base member 14. The holding member 12 generally includes an upper surface 16, a lower lip 18 having a top side 20 and a bottom side 22, and six sloping peripheral faces 24a-f extending between the upper surface 16 and the lower lip 18. The base member 14 has an upper surface 26 and a lower surface 28, each of which are provided with an adhesive 30, 32, respectively. The adhesive 30 on the upper surface 26 of the base member 14 couples the base member 14 to the bottom side 22 of the lower lip 16. Preferably, the remainder of the upper surface 26, that is, the portion of the upper surface surrounded by the lower lip 18, is also provided with the adhesive 30 to give the remainder of the upper surface a tacky quality. The adhesive 32 on the lower surface 28 of the base member 14 is preferably provided with a peel-away protective layer 34 which prevents the lower surface 28 of the base member 14 from unintentionally sticking to another surface, e.g., onto a surgical drape until the holder 10 is purposefully positioned for use. The peel-away protective layer 34 is easily removable by hand. Providing a means for adhering the holder 10 to a surface such as a surgical drape, facilitates single-handed use of the device and thereby allows a surgeon to keep one hand free while using the device.

Figure 3:
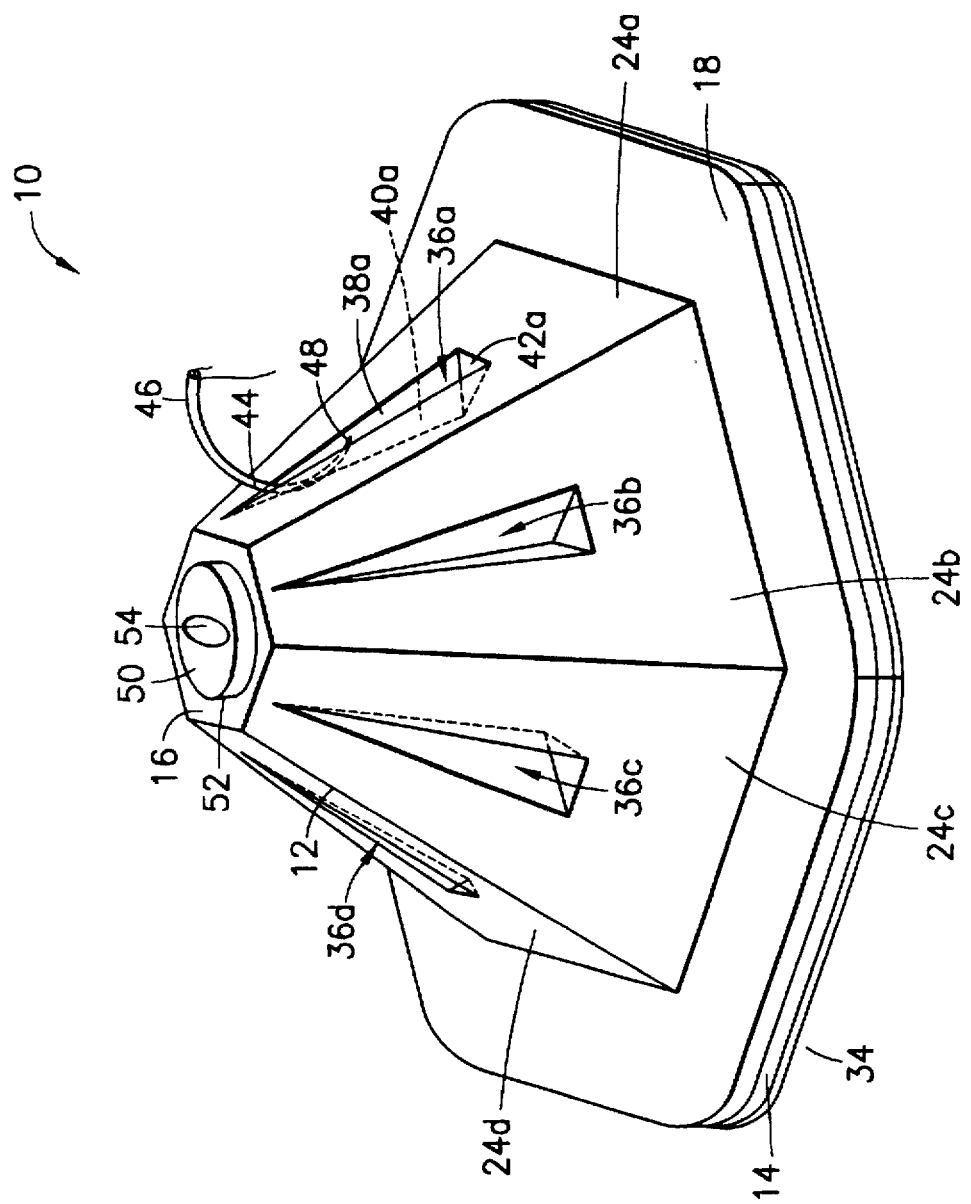
FIG. 3 is a perspective view of the suture needle holder of FIG. 1, shown with a suture needle being held by the holder.

According to a preferred aspect of the first embodiment, the holding member 12 is preferably vacuum-formed from clear PETG to be generally frusto-pyramidal in shape and, as stated above, and to have six faces 24a-24f sloping inward from the lower lip 18 to the upper surface 16. Each face 24a-f preferably has a needle park 36a-f provided thereon. With reference to needle park 36a, each needle park is preferably an inwardly formed portion of the holding member 12 having two adjoining walls 38a, 40a and a floor portion 42a which intersects the adjoining walls. The adjoining walls 38a, 40a are skewed to intersect at an acute angle, preferably approximately 2° to 20°. The depth of the needle park and the angle at which the adjoining walls intersect are both chosen such that when the shaft 44 of a suture needle 46 is inserted into the needle park, the walls 38a, 40a frictionally engage the shaft of the needle and hold the needle in the park 36a. As seen in FIG. 3, the sharp tip 48 of the suture needle need not contact the needle park when the needle is being held therein. It will also be appreciated that by providing a needle park 36a-f on each of the faces 24a-f, the holder 10 may be freely positioned relative to the operating position of a surgeon as one of the needle parks will always be positioned for use by the surgeon. The concern of whether the device will be aligned for optimal use by the surgeon is thereby eliminated.

By way of example, and with the understanding that other dimensions may also be used, dimensions for the suture needle holder are hereby provided. The suture needle holder has a height of approximately one to three inches. The holding member has a width across its bottom end, from the inside of the lip to the inside of the lip, of approximately two to four inches, and the base member has a width of approximately two and a half to five inches.

The upper surface 16 of the holding member 12 is preferably provided with a generally cylindrically-shaped raised portion 50 having a circumferential channel 52 around which suture material may be thread; i.e., the raised portion and channel may be used to assist a physician in tying off suture. Central in the raised portion 50, an opening 54 is provided through which used suture needles can be received into the interior of the holder 10. Preferably, the opening 54 includes a tapered entryway 56, which becomes smaller toward the base member 14 and thereby prevents suture needles from exiting through the opening. In addition, the disposed suture needles, e.g., suture needle 58, stick to the adhesive 30 on the upper surface 26 of the base member 14, further inhibiting any disposed suture needles from being released from within the holder 10 (FIG. 2).

Figure 4:
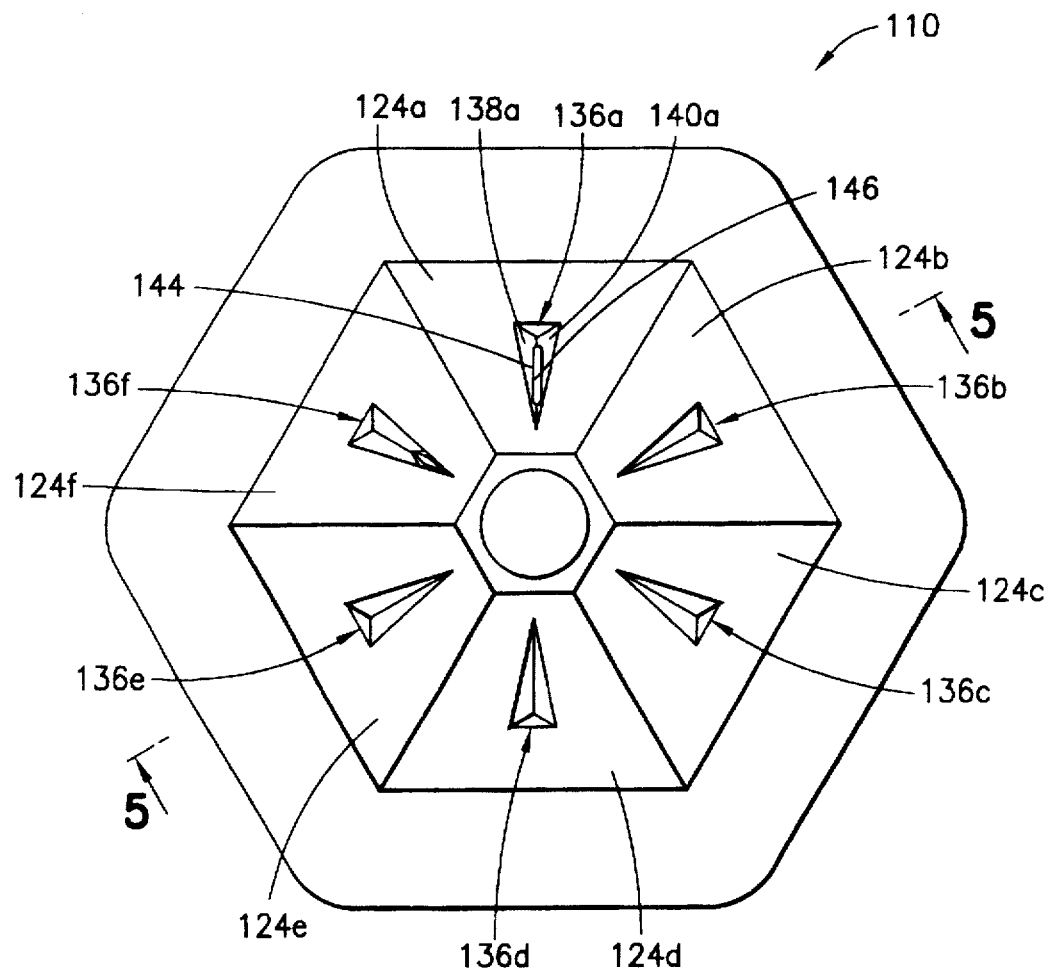
FIG. 4 is a top view of a second embodiment of a suture needle holder according to the invention.
Figure 5:
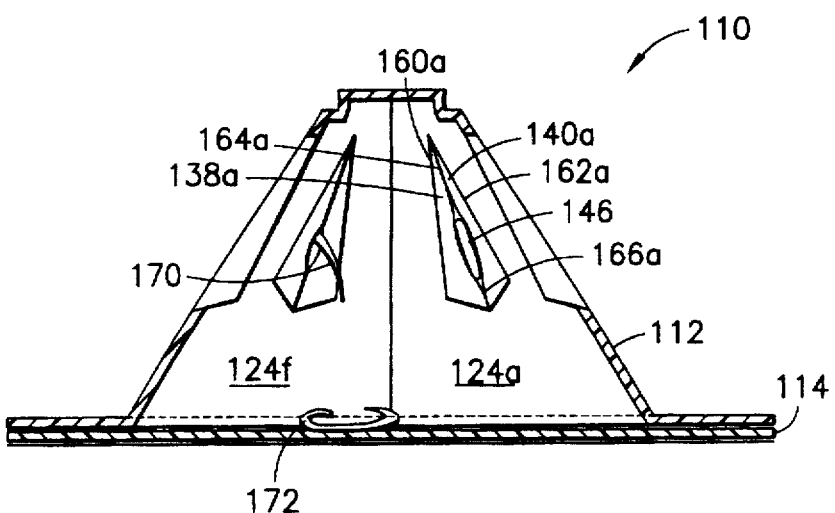
FIG. 5 is a cross-section through line 5—5 in FIG. 4.

Turning now to FIGS. 4 and 5, a second embodiment of a suture needle holder 110, substantially similar to the first embodiment (with like parts having numbers incremented by 100), is shown. The suture needle holder generally includes a hollow frustum-shaped holding member 112 and a base member 114 coupled to a lower portion of the holding member. The holding member 112 is provided with six sloping faces 124a-f, each of the faces being provided with a needle park 136a-f. With reference to needle park 136a, each needle park is generally formed from two walls 138a, 140a, each of which is angled relative to the face 124a, and each of which is preferably flexible. Each wall 138a, 140a has a first side 160a, 162a, coupled to a portion of the same sloping face 124a, and a second free side 164a, 166a. The free side 164a of one wall 138a is adjacent, but discontinuous, from the free side 166a of the other wall 140a. If desired, the free sides 164a, 166a may contact one another. A suture needle 144 is positionable between the walls 138a, 140a such that a portion of the shaft 146 is insertable between the free sides 164a, 166a of the walls 138a, 140a and stably held therebetween. It will be appreciated that by pushing a suture needle, e.g., suture needle 170, further through the walls, the suture needle can be pushed into the hollow holding member 12 and the walls, if resiliently flexible, will return to a closed position. Regardless, the suture needle, e.g., suture needle 172, will be safely enclosed within the hollow needle holder 110.

There have been described and illustrated herein embodiments of a suture needle holder. While particular embodiments of the invention have been described, it is not intended that the invention be limited thereto, as it is intended that the invention be as broad in scope as the art will allow and that the specification be read likewise. Thus, while particular shapes for the holding member have been disclosed, it will be appreciated that other shapes can be used as well. For example, the holding member may have fewer or more than six faces, or the holding member may be conically shaped. Furthermore while PETG has been disclosed as a suitable material for manufacturing the holding member, it will be understood that other materials, preferably vacuum-formable or injection moldable, can also be used. In addition, while each face is described as including a needle park, it will be appreciated that not all of the faces need be provided with a needle park. Moreover, it will be appreciated that, where a multi-faceted holding member (i.e., not a conical holding member) is used, the needle park may be provided at the corners formed by the faces rather than on the faces. Also, while a raised portion having a suture receiving channel is preferred, it will be recognized that the raised portion is not required. In addition, while the holding member has been shown as having a continuous peripherally extending lip, it will be appreciated that the lip may extend inward, or may be discontinuous. Furthermore, while it is preferable that the upper and lower sides of the base member be substantially completely provided with adhesives, it will be appreciated that an adhesive is not required on either side. Without any adhesive, the holding member and base member may be coupled in another manner, e.g., by stapling. Moreover, it will also be appreciated that an adhesive may be provided to the bottom side of the lower lip, and that the holding member may be provided directly to a surgical drape or other desired surface; i.e., without a base member positioned therebetween. In addition, while the holder has been described as being assembled from two primary components, i.e., the holding member and the base member, it will be understood that the holding member and base member can be formed or molded as a unitary member. Adhesive may be provided to the lower surface of a unitary formed holder. Furthermore, while the suture holder has been described with reference to holding suture needles, it will be appreciated that the suture holder may be used with other sharp surgical implements. It will therefore be appreciated by those skilled in the art that yet other modifications could be made to the provided invention without deviating from its spirit and scope as so claimed.

What is claimed is:

1. A holder and collector for at least one surgical implement having a shaft and a sharp tip, comprising:

a hollow holding portion having an exterior surface and an interior sized to hold a plurality of surgical implements, said exterior surface provided with at least one engagement means for frictionally engaging the shaft of one of the surgical implements and having an opening into said interior which permits at least one of the surgical implements to be provided completely into said interior.

2. A holder and collector according to claim 1, wherein: said holder portion is generally frustum-shaped.

3. A holder and collector according to claim 1, wherein: further comprising:

said holder portion is made from a clear material.

4. A holder and collector according to claim 1, further comprising:

a base portion,
wherein said holder portion is provided with a lower lip and said lower lip is coupled to said base portion.

5. A holder and collector according to claim 4, wherein: said base portion has an upper side and a lower side, said lower side being provided with an adhesive.

6. A holder and collector according to claim 1, wherein: said at least one engagement means is integrally formed with said holder portion.

7. A holder and collector according to claim 1, wherein: the holder portion is provided with a plurality of sloped faces, each of said sides having an engagement means.

8. A holder and collector according to claim 1, wherein: each of said engagement means is formed by respective first and second portions of said exterior surface, said first and second portions being acutely angled relative to each other such that the shaft of the surgical implement is frictionally engagable therebetween.

9. A holder and collector according to claim 1, wherein: said holder portion is preferably provided with a raised portion having a circumferential channel.

10. A holder and collector according to claim 1, wherein: said opening is provided with a tapered entrance.

11. A holder and collector according to claim 1, wherein: said at least one engagement means is formed from first and second wall portions, said first wall portion being angled relative to said exterior surface and having a first coupled side coupled to said exterior surface and a first free side, and said second wall portion being angled relative to said exterior surface and having a second coupled side coupled to said exterior surface and a second free side, said first and second free sides being adjacent to and discontinuous from each other such that the shaft of the surgical implement is positionable therebetween.

12. A holder and collector according to claim 1, wherein: said opening is provided between said first and second wall portions.

13. A holder and collector according to claim 4, wherein: said suture needle holder and collector has a height of approximately one to three inches, said interior has a largest dimension of approximately two to four inches, and said base portion has a width of approximately two and a half to five inches.

14. A holder and collector for at least one surgical implement having a shaft and a sharp tip, said holder and collector for use with a surgical drape, comprising:

a) a hollow plastic holding portion having an exterior surface and an interior sized to hold a plurality of surgical implements, said exterior surface provided with at least one engagement means for frictionally engaging the shaft of one of the surgical implements and having an opening into said interior which permits at least one of the surgical implements to be provided completely into said interior; and b) first means for attaching said holding portion to the surgical drape.

15. A holder and collector according to claim 14, wherein: said holding portion is a made from PETG.

16. A holder and collector according to claim 14, further comprising:

c) a base portion; and d) second means for attaching said base portion to said holder portion, said base portion being provided with said first means for attaching.

17. A holder and collector according to claim 16, wherein: said base portion is coupled to said has an upper side and a lower side, said lower side being provided with an adhesive.

18. A holder and collector according to claim 14, wherein said at least one engagement means is integrally molded with said holder portion.

19. A holder and collector according to claim 1, wherein: said holder portion is preferably provided with a raised portion having a circumferential channel.

20. A holder and collector according to claim 16, wherein: said suture needle holder and collector has a height of approximately one to three inches, said interior has a largest dimension of approximately two to four inches, and said base portion has a width of approximately two and a half to five inches.

* * * * *